(12) United States Patent
Münst et al.

(10) Patent No.: US 11,421,979 B2
(45) Date of Patent: Aug. 23, 2022

(54) METHOD FOR GENERATING A TWO-DIMENSIONAL INTERFEROGRAM USING A MICHELSON-TYPE OPEN-BEAM INTERFEROMETER

(71) Applicant: VISOTEC GMBH, Lübeck (DE)

(72) Inventors: Michael Münst, Lübeck (DE); Helge Sudkamp, Lübeck (DE); Peter Koch, Lübeck (DE); Gereon Hüttmann, Lübeck (DE)

(73) Assignee: VISOTEC GMBH, Lübeck (DE)

( * ) Notice: Subject to any disclaimer, the term of this patent is extended or adjusted under 35 U.S.C. 154(b) by 38 days.

(21) Appl. No.: 16/964,066

(22) PCT Filed: Jan. 25, 2019

(86) PCT No.: PCT/EP2019/051816
§ 371 (c)(1),
(2) Date: Jul. 22, 2020

(87) PCT Pub. No.: WO2019/145459
PCT Pub. Date: Aug. 1, 2019

(65) Prior Publication Data
US 2020/0393236 A1  Dec. 17, 2020

(30) Foreign Application Priority Data

Jan. 26, 2018 (DE) .................... 10 2018 101 768.5

(51) Int. Cl.
*G01B 9/02* (2022.01)
*G01B 9/02091* (2022.01)
(Continued)

(52) U.S. Cl.
CPC .......... *G01B 9/02091* (2013.01); *A61B 3/102* (2013.01); *A61B 3/12* (2013.01); *G01B 9/02032* (2013.01)

(58) Field of Classification Search
CPC .............. G01B 9/0209; G01B 9/02091; G01B 9/02032; A61B 3/102; A61B 3/12
See application file for complete search history.

(56) References Cited

U.S. PATENT DOCUMENTS

2014/0313477 A1* 10/2014 Raymond .......... G01N 21/4795
                                                                 351/206
2016/0345820 A1* 12/2016 Frisken ................. A61B 3/102

FOREIGN PATENT DOCUMENTS

WO    WO 2009/111609    9/2009
WO    WO 2017/029160    2/2017

OTHER PUBLICATIONS

Helge Sudkamp, Peter Koch, Hendrik Spahr, Dierck Hillmann, Gesa Franke, Michael Münst, Fred Reinholz, Reginald Birngruber, and Gereon Httmann, "In-vivo retinal imaging with off-axis full-field time-domain optical coherence tomography," Opt. Lett. 41, 4987-4990 (2016) (Year: 2016).*

(Continued)

*Primary Examiner* — Tarifur R Chowdhury
*Assistant Examiner* — Jonathon Cook
(74) *Attorney, Agent, or Firm* — Sheridan Ross P.C.

(57) ABSTRACT

The invention relates to a method for creating a two-dimensional interferogram with a Michelson-type free-beam interferometer, comprising an extended, partially spatially coherent light source and a two-dimensional light detector, wherein light from the light source is split by a beam splitter with a semitransparent beam splitter mirror into a sample light beam and a reference light beam and taken to a sample arm and a reference arm, wherein the sample light beam returning from a sample is directed by the beam splitter mirror onto the light detector, wherein the reference light beam emerging from the reference arm makes a predetermined angle greater than zero with the sample light beam on the light detector, and wherein the length of the reference (Continued)

arm is variable, where the reference light beam is directed by means of an odd number of reflections in each reflection plane in at least one reference arm section so that it is displaced laterally to itself and travels antiparallel through a light-deflecting element working by refraction or diffraction which is secured at the exit of the reference arm.

11 Claims, 2 Drawing Sheets

(51) Int. Cl.
*A61B 3/10* (2006.01)
*A61B 3/12* (2006.01)
*G01B 9/02015* (2022.01)

(56) References Cited

OTHER PUBLICATIONS

English Translation of the International Preliminary Report on Patentability for International (PCT) Patent Application No. PCT/EP2019/051816, dated Jul. 28, 2020, 7 pages.
Sudkamp et al. "In-vivo retinal imaging with off-axis full-field time-domain optical coherence tomography," Optics Letters, Nov. 2016, vol. 41, No. 21, pp. 4987-4990.
International Search Report and Written Opinion for International (PCT) Patent Application No. PCT/EP2019/051816, dated Mar. 11, 2019, 10 pages.
English Translation of International Search Report and Written Opinion for International (PCT) Patent Application No. PCT/EP2019/051816, dated Mar. 11, 2019, 8.

\* cited by examiner

METHOD FOR GENERATING A TWO-DIMENSIONAL INTERFEROGRAM USING A MICHELSON-TYPE OPEN-BEAM INTERFEROMETER

CROSS REFERENCE TO RELATED APPLICATIONS

This application is a national stage application under 35 U.S.C. 371 and claims the benefit of PCT Application No. PCT/EP2019/051816 having an international filing date of 25 Jan. 2019, which designated the United States, which PCT application claimed the benefit of German Patent Application No. 10 2018 101 768.5 filed 26 Jan. 2018, the disclosures of each of which are incorporated herein by reference in their entireties.

The invention relates to a method for creating a two-dimensional interferogram with a Michelson-type free-beam interferometer, comprising an extended, partially spatially coherent light source and a two-dimensional light detector, wherein light from the light source is split by a beam splitter with a semitransparent beam splitter mirror into a sample light beam and a reference light beam and taken to a sample arm and a reference arm of variable length.

By an extended, partially spatially coherent light source is meant here that the light source has a surface emitting a partially spatially coherent light, wherein light modes emitted from a first marginal surface region no longer interfere with light modes from a second marginal surface region situated opposite the first region, i.e., spaced apart from the first region by roughly a diameter of the surface. One example of such a light source is a non-fiber-coupled superluminescent diode (SLD).

Free-beam Michelson-type interferometers are used in devices for optical coherence tomography (OCT) and elsewhere, being designed to simultaneously detect all the light scattered by a two-dimensional sample ("full-field OCT, FF-OCT) and to match it with the lateral scattering sites on the sample. The publication WO 2017/029160 A1, which comes from the working group of the inventors, describes one such device and a corresponding measurement method.

In particular, the method and device of WO 2017/029160 A1 utilize partially spatially coherent light with short coherence length—less than 25 micrometers—from the NIR spectrum, and the free-beam interferometer comprises a reference arm whose length can be changed by a movable reference mirror. Interference on the two-dimensional light detector—such as a CCD or CMOS camera—at the exit from the interferometer will only occur if the optical wavelengths of reference light and scattered sample light are matched up within the coherence length. The variable reference arm thus allows bringing sample light from different sample depths to interfere with the reference light. The changing of the length of the reference arm can be realized by the movement of the reference mirror along the optical axis in the manner of the familiar "time-domain" (TD) OCT, wherein a repeating movement of the mirror is possible for repeated deep scans.

Scattered sample light that does not interfere with the reference light arrives at the light detector at the same time as the background. In order to separate the background from the interferogram in a post-processing and determine the phase and amplitude of the sample light, reference and sample light are superimposed on each other at a tilt by a predetermined angle, and the resulting distribution of the light intensity is then detected ("off-axis", OA). In this way, the interferogram comprises an additional pattern of interference bands along the detector surface. In the Fourier transform of the detected image data, the Fourier components associated with the interferogram are thus displaced by a predetermined k-vector relative to the Fourier coefficients of the background.

The device and the method of WO 2017/029160 A1, according to what has been stated above, are clearly distinguished from other OCT methods by the concept of "Off-Axis Full-Field Time-Domain OCT" (OA-FF-TD-OCT).

In the practical implementation of the teaching of WO 2017/029160 A1, especially based on its FIG. 1, the problem arises that a tilted reference mirror, while tilting the reference beam and directing it onto the light detector, also displaces it laterally with respect to the sample beam. This lateral displacement proves to be a problem in the case of meager design space for the optical arrangement and/or great length of the interferometer arms as compared to the beam diameter. The reference beam then no longer strikes the center of the detector.

If the OA-FF-TD-OCT method is used to examine the fundus of the eye, for technical reasons there results a sample arm length of several 100 mm. The reference arm must have this same optical length as the sample arm. For example, a typical spacing between the reference mirror and the light detector is 250 mm. The angle which the reference and the sample beam must comprise on the light detector in order to generate a detectable band pattern depends on the diameter of the individual light-sensitive pixels of the detector, such as 3.45 µm (Sony 252 sensor with 2045×1536 pixels), and on the central wavelength of the partially spatially coherent light source, such as 830 nm, and amounts to $\alpha \approx 3.5°$, for example. The lateral offset of the reference light relative to the sample light LS on the image sensor is $\Delta S = \tan \alpha \times l_R$ with $l_R$ being the spacing between the reference mirror (midpoint) and the image sensor. With the preceding exemplary values, there results on the light detector a lateral offset of 15.26 mm. The beam diameter would then have to have at least this 15.26 mm in addition to the detector size, around 7 mm, and a large portion of the light would not even be utilized. With partially spatially coherent light sources, there is also a reduction in the contrast of the interference signal, and thus the sensitivity and contrast range of the retinal images.

Furthermore, any movement of the reference mirror to change the reference arm length also results in a further change in the lateral offset at the light detector.

Therefore, the problem of the invention is to propose a method for interferometry with a Michelson-type free-beam interferometer in which the sample and the reference light can be superimposed at the light detector without a lateral offset and with a predetermined angle with each other greater than zero.

The problem is solved by a method for creating a two-dimensional interferogram with a Michelson-type free-beam interferometer, comprising an extended, partially spatially coherent light source and a two-dimensional light detector, wherein light from the light source is split by a beam splitter with a semitransparent beam splitter mirror into a sample light beam and a reference light beam and guided to a sample arm and a reference arm, wherein the sample light beam returning from a sample is directed by the beam splitter mirror onto the light detector, the reference light beam emerging from the reference arm makes a predetermined angle greater than zero with the sample light beam on the light detector, wherein the length of the reference arm is variable, characterized in that the reference light beam is directed by means of an odd number of reflections in each reflection plane in at least one reference arm section so that it is displaced laterally to itself and travels antiparallel through a light-deflecting element working by refraction or diffraction which is secured at the exit of the reference arm.

The dependent claims indicate advantageous embodiments.

It should first be noted that the described problems are quite easily avoidable in other interferometer types, such as a Mach-Zehnder interferometer. However, the Michelson interferometer is appealing on account of its simple design and the small number of optical components needed and is therefore especially attractive for the mass production of OCT systems.

In a classic Michelson interferometer, the reference beam is reflected onto itself by the reference mirror, and the entrance and exit of the reference arm thus coincide. In the present case, according to the invention, the entrance and exit of the reference arm are to be separated spatially, so that an additional optical element can be secured according to the invention at the exit in order to deflect the returning reference light by a predetermined angle. Since this predetermined angle only amounts to a few degrees, the light-deflecting element should bring about the deflection by means of diffraction or refraction, by not by reflection. The light-deflecting element can preferably be a prism or a diffraction grating.

If the reference light in the reference arm is directed such that it always impinges on the light-deflecting element at the same location and at the same angle, especially at any given length of the reference arm, then the diffracting or refracting element secured according to the invention can be adjusted so that the reference light constantly reaches the detector at the predetermined angle of deflection and with no lateral offset relative to the sample light.

The person skilled in the art is aware that retroreflectors can reflect the reference beam such that it travels antiparallel and laterally displaced from itself. These conditions may thus be accomplished with a retroreflector instead of the traditional reference mirror. Possible retroreflectors for this are the 90°-angled mirror or the classic corner cube, i.e., arrangements of two or three mirrors oriented at a 90° angle relative to each other.

According to the invention, at least one section of the reference arm should have this kind of path for the reference light. Preferably, the length of the reference arm in the at least one reference arm section is changed by having the reference light beam travel laterally displaced from itself and antiparallel. The reference arm length then does not affect the location or angle of the reference beam upon striking the light-deflecting element situated at the exit.

Unexpectedly, however, it turns out that a retroreflector is not suitable for implementing the invention. Namely, the interferograms will then be very weak or even vanishing toward the margins of the image.

The reason for this is the extended, partially spatially coherent light source.

If one uses the classic Michelson layout with zero angle between the sample and the reference light, one will obtain interference at all the pixels of the light detector, because both beam portions have been reflected exactly twice when reaching the detector, namely, once at the beam splitter and once at the reference mirror or at the sample. A retroreflector such as the 90°-angled mirror, however, performs two reflections, with the result that the reference beam emerging from the reference arm is mirror-inverted relative to the sample beam. Light components of the sample and the reference light which are incident on pixels on one side margin of the detector in fact come from two opposite margin areas of the two-dimensionally extending light source and therefore do not interfere.

This problem can be eliminated according to the invention in that the reference light beam is directed laterally displaced from itself and antiparallel by means of an odd number of reflections in each reflection plane in at least one reference arm section. Thus, for example, three reflections may be performed in one reflection plane in order to obtain a reference light suitable for interference with the sample light.

By the reflection plane is meant here a plane in space which is subtended by the normal direction of a flat mirror and the incidence or exiting direction of a light beam reflected by the flat mirror. The layout of the interferometer establishes all beam directions and mirror arrangements, i.e., all of the reflection planes are intrinsic to the design and known in advance. As a rule, one will provide only one reflection plane for the path of the reference light in the reference arm. However, at least one well-defined reflection plane is necessarily provided, since the reference beam must be laterally displaced between the entrance and the exit of the reference arm.

While a retroreflector in the style of a corner cube can perform three reflections, these will occur in at least two different reflection planes. Neither in this case is the emerging reference light suitable for the interference with the sample light on the entire detector.

However, if one performs an odd number of reflections in each reflection plane—such that there is more than one reflection—for the light in the reference arm, then the reference light can emerge reflected from the reference arm just as if there were only the single reflection in the traditional Michelson interferometer. The light-deflecting element additionally situated at the exit according to the invention then directs the reference beam at a predetermined angle relative to the sample beam onto a predetermined region of the light detector—usually the entire detector surface. The sample and the reference light can interfere on the entire light detector. The two beams do not need to be broader than the light detector. A change in the reference arm length has no impact on the lateral position of the reference beam at the detector.

On its path in the reference arm, the reference light can transmit as many diffracting or refracting optical components as desired and thereby undergo changes in beam direction. This has no further influence on its ability to interfere completely with the sample light, as long as there is only at least one reflection between the entrance and the exit of the reference arm.

The exact inversion of the reference beam direction with a lateral offset between the incoming and outgoing beam in the at least one reference arm section, provided preferably for changing the reference arm length, can be achieved in a variety of ways, not all of which need be presented here.

Instead, exemplary embodiments of interferometer arrangements implementing the method according to the invention shall be explained more closely with the aid of figures.

Figure 1:
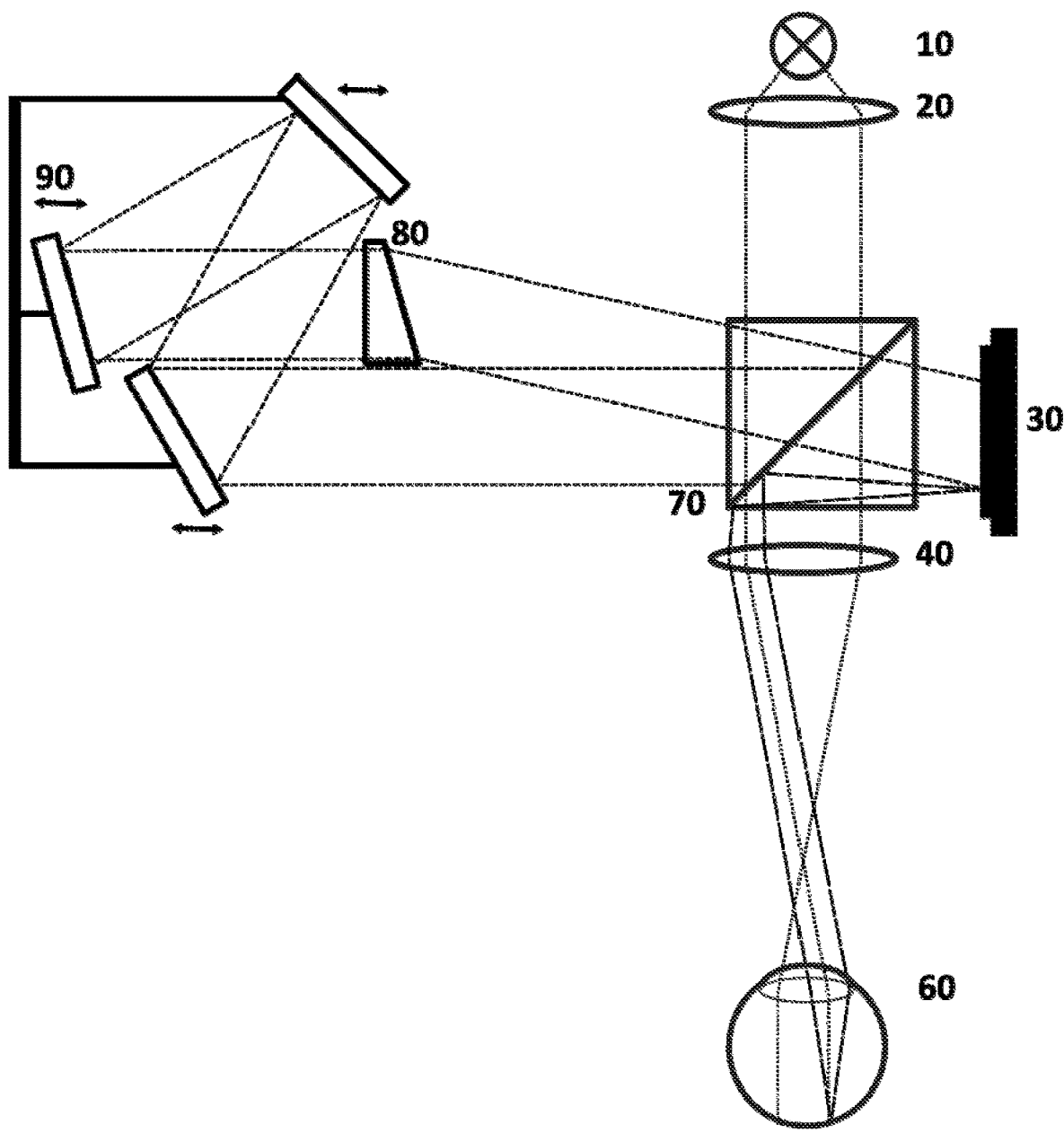
FIG. 1 shows an exemplary embodiment with three mirrors for the laterally displaced inversion of the beam direction and with a prism as the light-deflecting element.

FIG. 1 shows a Michelson-type free-beam interferometer, realizing the method according to the invention. The light of an extended, partially spatially coherent light source (10) is at first collimated by a collimation lens (20) and then divided by a beam splitter cube (70) into sample and reference light. The sample light is supposed to be directed onto the retina of a living eye (60) across the largest possible area. For this, focusing is performed with a focusing lens (40) in front of the eye (60), so that the biological lens refracts the divergent rays emerging from the focus in suitable manner. The sample light scattered by the retina is projected via the lens of the eye and the focusing lens (40) onto an electronic camera (30) under reflection at the beam splitter cube (70).

At the same time, the reference light beam is collimated by an arrangement (90) of three mirrors and directed in a single reflection plane common to the mirrors, so that it travels antiparallel and laterally displaced from itself. It then impinges on a prism (80), which refracts the beam and deflects it onto the two-dimensional light detector (30) at a predetermined angle relative to the sample light beam. The prism (80) here is fixed in place, while the arrangement (90) of the three mirrors is movable along the direction of entry or exit of the reference light beam. The lines of connection of the individual mirrors to a bar, as shown in FIG. 1, indicate here a common support system of the mirrors, which ensures that the mirrors retain their mutual arrangement even during the displacement. While this displacement of the arrangement (90) changes the length of the reference arm, it does not change the angle or the locus of incidence of the reference light on the light detector (30).

It is also evident from the beam paths depicted in FIG. 1 that light modes propagating behind the collimation lens (20), for example in the left marginal area of the light beam, are directed by both the sample arm and the reference arm into the lower marginal area of the detector (30). If, instead of the arrangement (90), there were a 90°-angled mirror as the retroreflector in the reference arm, these light modes would instead emerge from the sample arm in the lower and from the reference arm in the upper region of the detector (30).

It will be evident that one may also consider a variety of mirror arrangements, including ones with more than three mirrors, in which the normals of all the mirrors lie in a common plane, wherein the incident light is directed along this plane to produce a laterally displaced and antiparallel-running light beam. However, only those variants in which the light beam experiences an odd number of reflections altogether are serviceable for interferometry with an extended, partially spatially coherent light source according to the invention.

Figure 2:
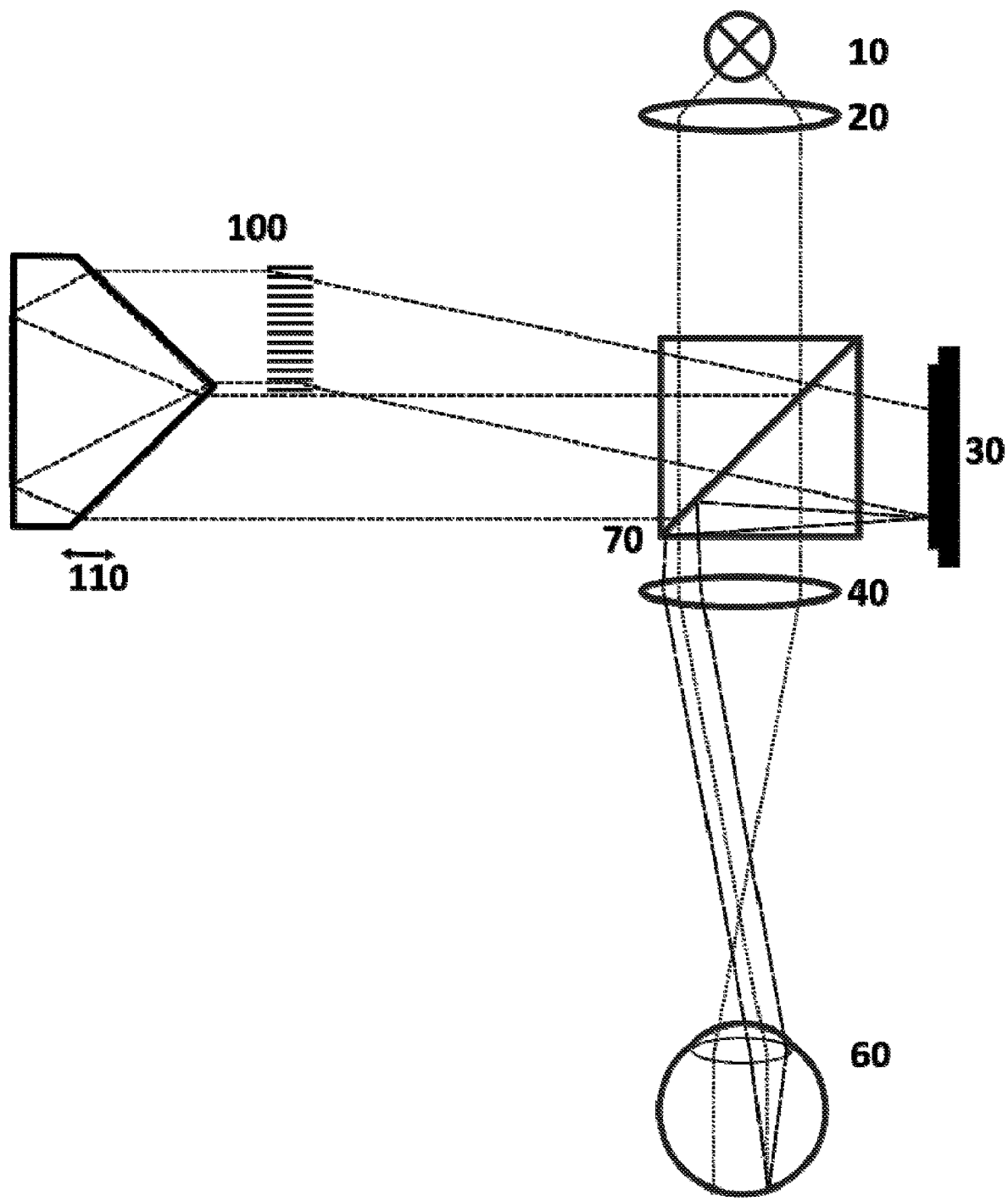
FIG. 2 shows an exemplary embodiment having a prism with two light-diffracting surfaces and one reflecting surface for the laterally displaced inversion of the beam direction and with a diffraction grating as the light-deflecting element.

FIG. 2 shows a second, quite simple and therefore preferred embodiment of the reference arm implementing the method according to the invention. The other components of the free-beam interferometer are the same as in FIG. 1.

The laterally offset and antiparallel running path of the reference light beam can also be accomplished with just one mirror, but the light here does not impinge perpendicular on the mirror. For example, the reference light beam in FIG. 2 is refracted and deflected by a first optically transparent surface of a prism (110), taken through the prism (110) onto a reflective surface of the prism (110) and reflected, and finally refracted once more by a second transparent surface so that the emerging reference beam is laterally displaced and antiparallel with respect to the incoming beam. It is obviously advantageous to have a symmetrical design for the prism (110), as shown in FIG. 2. Furthermore, the refracting surfaces and the reflecting surface should form a structural unit, so that they can perform a common movement—indicated by double arrow—along the reference beam direction without altering the arrangement relative to each other.

It is generally advantageous for the reference beam to be refracted at least twice and reflected exactly once with a prism and a mirror in the same plane. The plane here is the common refraction and reflection plane, wherein a refraction plane is subtended by analogy with the reflection plane by the beam direction and the normals of the refractive surface. Furthermore, it is considered advantageous to use a prism (110) with a reflective coating on at least one lateral surface.

However, many alternative configurations are possible, e.g., those in which no symmetrical prism is used. Neither is it absolutely necessary to use a reflective prism. The mirror, for example, may also be arranged at a predetermined distance behind the rear, transparent surface of a prism. In this case, the reference light beam will leave the entirely transparent prism at the rear side, travel through an air gap, and then be reflected. On its path in the reference arm it will be refracted a total of at least four times and reflected once.

An air gap may be a disadvantage in terms of apparatus, because additional reflections with delayed travel time will also be produced at each boundary surface through which the light passes, which may have a disruptive effect at the latest during the interference with the sample light. But the transmission of the reference light through a refractive medium also generally produces chromatic dispersion, which is likewise undesirable. One will strive to keep the path length of the reference light through the refractive medium as short as possible.

In any case, the choice of the material of the prism and its design, i.e., the arrangement of the refractive surfaces and the precisely one mirror, may be quite diverse and in an individual instance will be subject to compromise and optimization considerations also taking into account the wavelengths being used.

Finally, there is shown in FIG. 2 a fixed diffraction grating (100) as the light-deflecting element in transmission. By contrast with the prism of FIG. 1, the grating (100) does not deflect the entire reference light by a predetermined angle, but rather it produces a divergent pencil of reference beams exiting from the grating (100) in the secondary diffraction maxima and the non-deflected beam in the principal maximum of zeroth order. If one uses the grating (100) for example to direct a beam toward the light detector (30) in the direction of a secondary maximum of first order, it must be considered that, because of the beam width, beams of the pencil in all the other diffraction orders can no longer reach the detector (30). This means that the grating (100) needs to be arranged at a minimum distance from the detector (30), the size of which can be easily determined through geometry.

What is claimed is:

1. A method for creating a two-dimensional interferogram, the method comprising:
    providing a Michelson-type free-beam interferometer comprising an extended, partially spatially coherent light source and a two-dimensional light detector;
    splitting, by a beam splitter with a semitransparent beam splitter mirror, light from the light source into a sample light beam for a sample arm and a reference light beam for a reference arm;
    directing, by the beam splitter mirror, the sample light beam returning from a sample onto the light detector, wherein the reference light beam emerging from the reference arm makes a predetermined angle greater than zero with the sample light beam on the light detector, wherein a length of the reference arm is variable; and reflecting, in at least one reference arm section, the reference light beam, an odd number of times so that the reference light beam is displaced laterally from itself and travels antiparallel through a light-deflecting element working by refraction or diffraction which is secured at an exit of the reference arm.

2. The method according to claim 1, further comprising changing the length of the reference arm in the at least one reference arm section so that the reference light beam travels laterally displaced from itself and travels antiparallel to the light detector through the light-deflecting element.

3. The method according to claim 2, wherein the reference light beam is directed through a prism or diffraction grating behind the at least one reference arm section.

4. The method according to claim 1, wherein the reference light beam is reflected in the at least one reference arm section across three mirrors.

5. The method according to claim 1, wherein the reference light beam is refracted at least twice and reflected precisely once by a prism and a mirror.

6. The method according to claim 5, wherein the prism comprises a reflective coating on at least one lateral surface.

7. A device, comprising;
a Michelson-type free-beam interferometer comprising:
an extended, partially spatially coherent light source; and
a two-dimensional light detector;
a beam splitter with a semitransparent beam splitter mirror that splits light from the light source into a sample light beam for a sample arm and a reference light beam for a reference arm, wherein the sample light beam returning from a sample is directed by the beam splitter mirror onto the light detector, wherein the reference light beam emerging from the reference arm makes a predetermined angle greater than zero with the sample light beam on the light detector, wherein a length of the reference arm is variable; and a light-deflecting element secured at an exit of the reference arm and working by refraction or diffraction, wherein the reference light beam is directed by means of an odd number of reflections in at least one reference arm section so that the reference light beam is displaced laterally from itself and travels antiparallel to the light source through the light-deflecting element.

8. The device according to claim 7, wherein at least one reference arm section comprises at least three mirrors, wherein the reference light beam is reflected by at least three mirrors.

9. The device according to claim 7, further comprising a prism and a mirror, wherein the reference light beam is refracted at least twice and reflected precisely once with the prism and the mirror.

10. The device according to claim 9, wherein the prism has a reflective coating on at least one lateral surface.

11. A method for creating a two-dimensional interferogram, the method comprising;
providing a Michelson-type free-beam interferometer comprising an extended, partially spatially coherent light source and a two-dimensional light detector;
splitting by a beam splitter with a semitransparent beam splitter mirror, light from the light source into a sample light beam from a sample arm and a reference light beam for a reference arm;
directing, by the beam splitter mirror, the sample light beam returning from a sample onto the light detector, wherein the reference light beam emerging from the reference arm makes a predetermined angle greater than zero with the sample beam on the light detector, wherein a length of the reference arm is variable: and
reflecting, in at least one reference arm section, the reference light beam an odd number of times so that the reference light beam is displaced laterally from itself and travels antiparallel through a light-deflecting element working by refraction or diffraction which is secured at an exit of the reference arm, and wherein the reference light beam is reflected by three mirrors in the at least one reference arm section.

* * * * *